United States Patent [19]

Meyer et al.

[11] 3,932,646

[45] Jan. 13, 1976

[54] PHARMACEUTICAL COMPOSITIONS CONTAINING UNSYMMETRICAL ESTERS OF 1,4-DIHYDROPYRIDINE 3,5-DICARBOXYLATE

[75] Inventors: Horst Meyer; Friedrich Bossert, both of Wuppertal-Elberfeld; Wulf Vater, Opladen; Kurt Stoepel, Wuppertal-Vohwinkel, all of Germany

[73] Assignee: Farbenfabriken Bayer AG, Germany

[22] Filed: Sept. 21, 1973

[21] Appl. No.: 399,387

Related U.S. Application Data

[62] Division of Ser. No. 242,238, April 7, 1972, Pat. No. 3,799,936.

[30] Foreign Application Priority Data

Apr. 10, 1971   Germany............................ 2117572

[52] U.S. Cl.................................. 424/266; 424/263

[51] Int. Cl.$^2$....................................... A61K 31/455
[58] Field of Search........................... 424/263, 266

[56] References Cited
UNITED STATES PATENTS
3,470,297   9/1969   Bossert et al. ...................... 424/263

*Primary Examiner*—V. D. Turner

[57] ABSTRACT

Pharmaceutical compositions containing unsymmetrical esters of 1,4-dihydropyridine 3,5-dicarboxylate as the active ingredient and methods of using same. The said ingredients are unsymmetrical esters of 1,4-dihydropyridine 3,5-dicarboxylic acid which are substituted at position-4 of the dihydropyridine ring by phenyl or a substituted phenyl moiety. The compositions have cardiovascular activity which makes them useful for effecting coronary vascular dilation and in the treatment of hypertension.

46 Claims, No Drawings

PHARMACEUTICAL COMPOSITIONS CONTAINING UNSYMMETRICAL ESTERS OF 1,4-DIHYDROPYRIDINE 3,5-DICARBOXYLATE

This is a division of application Ser. No. 242,238 filed Apr. 7, 1972 now U.S. Pat. No. 3,799,936 dated Mar. 26, 1974.

The present invention relates to unsymmetrical esters of 1,4-dihydropyridine-dicarboxylic acids, to processes for their production and to their use as coronary and antihypertensive agents.

Although a variety of esters of 4-substituted-1,4-dihydropyridine-3,5-dicarboxylic acids are known [see for example Knoevenagel, Ber. 31, 743 (1898) and U.S. Pat. Nos. 3,325,505; 3,441,648; 3,485,847; 3,488,359 and 3,511,847], all of these have been symmetrical with respect to the ester groups in the 3- and 5-positions. Indeed up to the present, the preparative methods available to the art for such esters were limited to the preparation of symmetrical esters.

The present invention is directed at compounds of the formula:

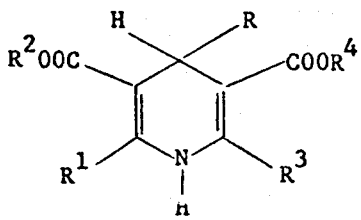

wherein
R is phenyl, unsubstituted or substituted by up to three substituents selected from the group consisting of lower alkyl, lower alkoxy, halogeno, trifluoromethyl or carbo(lower alkoxy);
$R^1$ and $R^3$, independent of the other, is hydrogen or lower alkyl;
$R^2$ is a member selected from the group consisting of lower alkyl, lower alkenyl, lower alkynyl, or lower alkoxy(lower alkyl);
$R^4$ is a member different from $R^2$ selected from the group consisting of lower alkenyl, lower alkynyl or lower alkoxy(lower alkyl),
or a pharmaceutically acceptable acid addition salt thereof.

The term alkyl denotes a univalent saturated branched or straight hydrocarbon chain containing from 1 to 18 carbon atoms. Representative of such alkyl groups are thus methyl, ethyl, propyl, isopropyl, butyl, isobutyl, sec.butyl, tert.butyl, pentyl, isopentyl, neopentyl, tert.pentyl, hexyl, isohexyl, heptyl, octyl, nonyl, decyl, undecyl, dodecyl, tridecyl, tetradecyl, pentadecyl, hexadecyl, heptadecyl, octadecyl, and the like.

The term lower alkyl denotes a univalent saturated branched or straight hydrocarbon chain containing from 1 to 6 carbon atoms. Representative of such lower alkyl groups are thus methyl, ethyl, propyl, isopropyl, butyl, isobutyl, sec.butyl, tert.butyl, pentyl, isopentyl, neopentyl, tert.pentyl, hexyl, and the like.

The term lower alkenyl denotes a univalent branched or straight hydrocarbon chain containing from 2 to 6 carbon atoms and nonterminal ethylenic unsaturation as, for example, vinyl, allyl, isopropenyl, 2-butenyl, 3-methyl-2-butenyl, 2-pentenyl, 3-pentenyl, 2-hexanyl, 4-hexenyl, and the like.

The term lower alkynyl denotes a univalent branched or straight hydrocarbon chain containing from 2 to 6 carbon atoms and nonterminal acetylenic unsaturation as, for example, ethynyl, 2-propynyl, 4-pentynyl, and the like.

As indicated, the present invention also pertains to the physiologically acceptable non-toxic acid addition salts of these basic compounds. Such salts include those derived from organic and inorganic acids such as, without limitation, hydrochloric acid, hydrobromic acid, phosphoric acid, sulfuric acid, methane sulphonic acid, acetic acid, tartaric acid, lactic acid, succinic acid, citric acid, malic acid, maleic acid, sorbic acid, aconitic acid, salicylic acid, phthalic acid, embonic acid, enanthic acid, and the like.

The compounds of the present invention can exist as optical isomers and both the racemates of these isomers and the individual isomers themselves are within the scope of the present invention. The racemates can be separated into their individual isomers through the well known technique and forming diastereoisomeric salts with optically active acids.

As discussed in greater detail below, the compounds of the present invention are valuable cardiovascular agents possessing in particular coronary vascular dilation properties together with antihypertensive properties.

These compounds are prepared through treatment of an ylidene-β-ketocarboxylic acid of the formula:

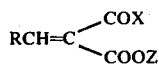

with either (a) an enaminocarboxylic acid ester of the formula:

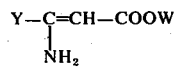

or (b) a β-ketocarboxylic acid ester of the formula:
Y—COCH$_2$COOW
and ammonia. In the foregoing formulas, X corresponds to one of $R^1$ and $R^3$ and Y corresponds to the other of $R^1$ and $R^3$ while Z corresponds to one of $R^2$ and $R^4$ and W corresponds to the other of $R^2$ and $R^4$.

The foregoing processes can be diagrammatically depicted as follows:

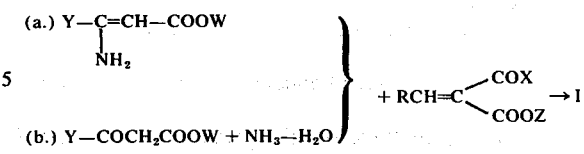

The process of the invention are generally carried out utilizing water or any inert organic solvent as diluent. Preferred organic solvents for this purpose include alcohols, such as methanol, ethanol and propanol, ethers such as dioxane, diethylether or tetrahydrofuran. Highly polar solvents such as glacial acetic acid, pyridine, dimethylformamide, dimethylsulfoxide and acetonitrile can also be employed. The reaction temperatures can be varied over a substantial range but in general, the reaction is carried out at from about 20° to about 200°C. Conveniently the reaction is conducted at the boiling point of the solvent. Either normal pressure or elevated pressure can be employed, normal pressure being more convenient. With the exception of ammonia which is generally used in excess, the reactants are employed in approximately stoichiometric amounts.

The requisite starting materials are either known to the art or can be readily prepared through conventional synthetic methods. As representative starting materials can be mentioned a. Ylidene-β-ketocarboxylic acids 2′, 3′- or 4′-Methoxybenzylideneacetoacetic acid ethyl ester, 2′, 3′- or 4′-methoxybenzylideneacetoacetic acid methyl ester, 2′-methoxybenzylideneacetoacetic acid allyl ester, 2′-methoxybenzylideneacetoacetic acid propargyl ester, 2′-methoxybenzylideneacetoacetic acid β-methoxyethyl ester, 2′-isopropoxybenzylideneacetoacetic acid ethyl ester, 3′-butoxybenzylideneacetoacetic acid methyl ester, 3′, 4′, 5′-trimethoxybenzylideneacetoacetic acid ethyl ester, 2′-methyl-β-benzylidenepropionylacetic acid methyl ester, 2′, 3′ or 4′-methylbenzylideneacetoacetic acid ethyl ester, 2′-methylbenzylideneacetoacetic acid β-ethoxyethyl ester, 2′-methylbenzylideneacetoacetic acid β-propoxyethyl ester, 3′, 4′-dimethoxy-5′-bromobenzylideneacetoacetic acid ethyl ester, 2′, 3′ or 4′-chloro/bromo/fluorobenzylideneacetoacetic acid ethyl ester, 2′-fluorobenzylideneacetoacetic acid methyl ester, 3′-chlorobenzylideneacetoacetic acid ethyl ester, 2′-chlorobenzylideneacetoacetic acid allyl ester, 2′-chloro-α-benzylidenepropionylacetic acid ethyl ester, 2′, 3′- or 4′-trifluoromethylbenzylideneacetoacetic acid ethyl ester, 2′-trifluoromethylbenzylideneacetoacetic acid propyl ester, 2′-trifluoromethylbenzylideneacetoacetic acid isopropyl ester, 2′-trifluoromethyl-α-benzylidenepropionylacetic acid ethyl ester, 2′-trifluoromethylbenzylideneacetoacetic acid propargyl ester, 3′-trifluoromethylbenzylideneacetic acid methyl ester, 2′-carboethoxybenzylideneacetoacetic acid ethyl ester, 3′-carboxymethylbenzylideneacetoacetic acid ethyl ester, 4′-carboxyisopropylbenzylidenacetoacetic acid isopropyl ester, and 4′-carboxymethylbenzylideneacetoacetic acid allyl ester.

b. β-Ketocarboxylic acid esters
Formylacetic acid ethyl ester,
acetoacetic acid methyl ester,
acetoacetic acid ethyl ester,
acetoacetic acid propyl ester,
acetoacetic acid isopropyl ester,
acetoacetic acid butyl ester,
acetoacetic acid t-butyl ester,
acetoacetic acid (α- or β-)-methoxyethyl ester,
acetoacetic acid (α- or β-)-ethoxyethyl ester,
acetoacetic acid (α- or β-)-propoxyethyl ester,
acetoacetic acid (α- or β-)-hydroxyethyl ester,
acetoacetic acid allyl ester,
acetoacetic acid propargyl ester,
acetoacetic acid cyclohexyl ester,
propionylacetic acid methyl ester,
propionylacetic acid ethyl ester,
propionylacetic acid isopropyl ester and
butyrylacetic acid ethyl ester.

c. Enaminocarboxylic acid esters
β-Aminocrotonic acid methyl ester,
β-aminocrotonic acid ethyl ester,
β-aminocrotonic acid isopropyl ester,
β-aminocrotonic acid propyl ester,
β-aminocrotonic acid allyl ester,
β-aminocrotonic acid butyl ester,
β-aminocrotonic acid β-methoxyethyl ester,
β-aminocrotonic acid β-ethoxyethyl ester,
β-aminocrotonic acid β-propoxyethyl ester,
β-aminocrotonic acid t-butyl ester,
β-aminocrotonic acid cyclohexyl ester and
β-amino-β-ethylacrylic acid ethyl ester.

Typical compounds of the present invention include:

2,6-Dimethyl-4-(2′-trifluoromethylphenyl)-1,4-dihydropyridine-3,5-dicarboxylic acid 3-methyl ester 5-allyl ester.

2,6-Dimethyl-4(2′-trifluoromethylphenyl)-1,4-dihydropyridine-3,5-dicarboxylic acid 3-ethyl ester 5-β-methoxyethyl ester.

2,6-Dimethyl-4-(2′-trifluoromethylphenyl)-1,4-dihydropyridine-3,5-dicarboxylic acid 3-ethyl ester 5-propargyl ester.

2-Methyl-6-ethyl-4-(2′-trifluoromethylphenyl)-1,4-dihydropyridine-3,5-dicarboxylic acid 3-β-propoxyethyl ester 5-methyl ester.

2-Methyl-6-isopropyl-4-(2′-fluorophenyl)-1,4-dihydropyridine-3,5-dicarboxylic acid 3-methyl ester 5-allyl ester.

2,6-Dimethyl-4-(2′-chlorophenyl)-1,4-dihydropyridine-3,5-dicarboxylic acid 3-isopropyl ester 5-propargyl ester.

2,6-Dimethyl-4-(2′-ethoxyphenyl)-1,4-dihydropyridine-3,5-dicarboxylic acid 3-allyl ester 5-propargyl ester.

2,6-Dimethyl-4-(3′-trifluoromethylphenyl)-1,4-dihydropyridine-3,5-dicarboxylic acid 3-propargyl ester 5-β-methoxyethyl ester.

2,6-Dimethyl-4-(3′-trifluoromethylphenyl)-1,4-dihydropyridine-3,5-dicarboxylic acid 3-ethyl ester 5-allyl ester.

2,6-Dimethyl-4-(3′-trifluromethylphenyl)-1,4-dihydropyridine-3,5-dicarboxylic acid 3-methyl ester 5-propargyl ester.

2,6-Dimethyl-4-(3′-trifluoromethylphenyl)-1,4-dihydropyridine-3,5-dicarboxylic acid 3-ethyl ester 5-β-ethoxyethyl ester.

2,6-Dimethyl-4-(3′-carboethoxyphenyl)-1,4-dihydropyridine-3,5-dicarboxylic acid 3-isopropyl ester 5-propargyl ester.

As previously stated, the compounds of this invention are valuable cardiovascular agents. In particular, the compounds upon administration cause a distinct and long-lasting dilation of the coronary vessels with a simultaneous nitrite-like reduction on the workload of the heart. At the same time, an anti-fibrillation effect and spasmolytic activity can be observed, the latter often manifesting itself not only in the smooth vascular muscle but also in the smooth muscle of the stomach, intestinal tract, urogenital tract and respiratory system. The compounds also exhibit hypotensive properties in the normo- and hypertonic animal.

The dose administered must of course be carefully adjusted to the age, weight and condition of the individual being treated, as well as the route of administration, dosage form and regimen, and the result desired. A satisfactory result can, in certain instances, be obtained at a dose as low as 0.0005 mg/kg i.v. and 0.01 mg/kg p.o. The upper limit of the dosage range is about 10 mg/kg i.v. and 100 mg/kg p.o. Preferred ranges are from about 0.001 to about 1 mg/kg i.v. and from about 0.1 to about 10 mg/kg p.o.

In general it has proved advantageous to administer the dose divided among several administrations in order to achieve effective results. At times it is of course necessary to depart from these amounts, and in particular to do so as a function of the body weight of the test animal, the route of administration, the animal and its individual behavior towards the medicine, the type of its formulation, and/or the time or interval of administration. In some cases less than the minimum amount will suffice while in others, the upper limit must be exceeded.

The compounds of the present invention are administered parenterally or orally in any of the usual pharmaceutical forms. These include solid and liquid oral unit dosage forms such as tablets, capsules, powders, suspensions, solutions, syrups and the like, including sustained release preparations, and fluid injectable forms such as sterile solutions and suspensions. The term unit dosage form as used in this specification and the claims refer to physically discrete units to be administered in single or multiple dosage to animals, each unit containing a predetermined quantity of active material in association with the required diluent, carrier or vehicle. The quantity of active material is that calculated to produce the desired therapeutic effect upon administration of one or more of such units.

Powders are prepared by comminuting the compound to a suitable fine size and mixing with a similarly comminuted diluent pharmaceutical carrier such as an edible carbohydrate material as for example, starch. Sweetening, flavoring, preservative, dispersing and coloring agents can also be present.

Capsules are made by preparing a powder mixture as described above and filling formed gelatin sheaths. A lubricant such as talc, magnesium stearate and calcium stearate can be added to the powder mixture as an adjuvant before the filling operation; a glidant such as colloidal silica may be added to improve flow properties; a disintegrating or solubilizing agent may be added to improve the availability of the medicament when the capsule is ingested.

Tablets are made by preparing a powder mixture, granulating or slugging, adding a lubricant and disintegrant and pressing into tablets. A powder mixture is prepared by mixing the compound, suitably comminuted, with a diluent or base such as starch, sucrose, kaolin, dicalcium phosphate and the like. The powder mixture can be granulated by wetting with a binder such as syrup, starch paste, acacia mucilage or solutions of cellulosic or polymeric materials and forcing through a screen. As an alternative to granulating, the powder mixture can be run through the tablet machine and the resulting imperfectly formed slugs broken into granules. The granules can be lubricated to prevent sticking to the tablet forming dies by means of the addition of stearic acid, a stearate salt, talc or mineral oil. The lubricated mixture is then compressed into tablets. The medicaments can also be combined with free flowing inert carriers and compressed into tablets directly without going through the granulating or slugging steps. A protective coating consisting of a sealing coat of shellac, a coating of sugar or polymeric material and a polish coating of wax can be provided. Dyestuffs can be added to these coatings to distinguish different unit dosages.

Oral fluids such as syrups and elixirs can be prepared in unit dosage form so that a given quantity, e.g., a teaspoonful, contains a predetermined amount of the compound. Syrups can be prepared by dissolving the compound in a suitably flavored aqueous sucrose solution while elixirs are prepared through the use of a non-toxic alcoholic vehicle. Suspensions can be formulated by dispersing the compound in a non-toxic vehicle in which it is insoluble.

Fluid unit dosage forms for parenteral administration can be prepared by suspending or dissolving a measured amount of the compound in a non-toxic liquid vehicle suitable for injection such as an aqueous or oleaginuous medium and sterilizing the suspension or solution. Alternatively a measured amount of the compound is placed in a vial and the vial and its contents are sterilized and sealed. An accompanying vial or vehicle can be proved for mixing prior to administration.

The pharmaceutical compositions of the invention can also contain other non-toxic adjuvants and modifiers such as dyes, buffering agents, preservatives, surfactants, emulsifiers, such as nonionic and anionic emulsifiers as, for example, polyoxyethylene-fatty acid esters, polyoxyethylene-fatty alcohol ethers, alkylsulphonates and arylsulphonates, or dispersing agents as, for example, lignin, sulfite waste lyes, methylcellulose, starch and polyvinyl pyrrolidone, perfumes, flavoring agents, preservatives and biocides.

Pharmaceutical compositions adapted for oral administration employ such ingredients as diluents and carriers, excipients and lubricants, as glucose, lactose, sucrose, corn and potato starch, sodium carboxymethyl cellulose, ethyl cellulose, cellulose acetate, powdered gum tragacanth, gelatin, alginic acid, agar, stearic acid, sodium, calcium and magnesium stearates, sodium lauryl sulfate, polyvinylpyrrolidone, sodium citrate, calcium carbonate, and dicalcium phosphate.

Pharmaceutical compositions adapted for parenteral injection employ such diluents and carriers as water and water-miscible organic solvents, in particular sesame oil, groundnut oil, aqueous propylene glycol, and N,N'-dimethylformamide. Examples of pharmaceutical compositions of the invention adapted for parenteral administration include sterile isotonic saline aqueous solutions of the active ingredient, which can be buffered with a pharmaceutically acceptable buffer and are preferably pyrogen free.

The pharmacological properties of these compounds are conveniently observed in well-known animal models which parallel the desired clinical response. Similarly toxicity is low, as measured for example in the conventional $LD_{50}$ determination. This can be seen in the following table:

| Compound of Example | Toxicity (Mouse) LD$_{50}$ mg/kg p.o. | Blood pressure effect on hypertensive rat mg/kg p.o. |
| --- | --- | --- |
| 1 | >3000 | from 10.0 |
| 2 | 800 | from 10.0 |
| 3 | 800 | from 3.1 |
| 4 | 200 | from 1.0 |
| 5 | 630 | from 3.1 |
| 6 | 200 | from 0.3 |
| 7 | >3000 | from 31.5 |
| 8 | 630 | from 1.0 |
| 9 | 3000 | |
| 10 | >3000 | |
| 11 | >3000 | from 10.0 |
| 12 | 100 | from 0.3 |
| 13 | 2000 | from 1.0 |
| 14 | 1000 | from 3.1 |
| 15 | >3000 | from 3.1 |
| 16 | 200 | from 10.0 |
| 17 | >3000 | from 10.0 |
| 18 | 3000 | from 10.0 |
| 19 | 3000 | |

The low dosages at which favorable hypotensive response is observed is also seen in the dosages at which a coronary effect is observed, as can be seen from the following tabulation:

| Compound of Example No. | Dose mg/kg i.v. |
| --- | --- |
| 1 | 0.05 |
| 2 | 0.01 |
| 3 | 0.01 |
| 4 | 0.005 |
| 5 | 0.001 |
| 6 | 0.005 |
| 7 | 0.05 |
| 8 | 0.01 |
| 10 | 5 |
| 11 | 0.05 |
| 12 | 0.003 |
| 13 | 0.05 |
| 14 | 0.01 |
| 15 | 0.05 |
| 16 | 0.05 |
| 17 | 0.01 |
| 18 | 0.05 |
| 19 | 2 to 5 |
| 20 | 2 to 5 |

The following examples will serve to further typify the nature of this invention without being a limitation on the scope thereof, the scope being defined solely by the appended claims.

EXAMPLE 1

Boiling a solution of 11.6 g of 2'-methylbenzylideneacetoacetic acid ethyl ester and 7.1 g of β-aminocrotonic acid allyl ester in 50 ml of ethanol for 10 hours yielded 2,6-dimethyl-4-(2'-methylphenyl)-1,4-dihydropyridine-3,5-dicarboxylic acid 3-ethyl ester-5-allyl ester of melting point 105° (from petroleum ether-/ethyl acetate). Yield 46% of theory.

EXAMPLE 2

Heating a solution of 11.6 g of 2'-methylbenzylideneacetoacetic acid ethyl ester, 7.0 g of acetoacetic acid propargyl ester and 6 ml of concentrated ammonia in 50 ml of methanol for 8 hours yielded 2,6-dimethyl-4-(2'-methylphenyl)-1,4-dihydropyridine-3,5-dicarboxylic acid 3-ethyl ester-5-propargyl ester of melting point 129° (from ethanol/H$_2$O). Yield 54% of theory.

EXAMPLE 3

Heating 11.1 g of 2'-fluorobenzylideneacetoacetic acid methyl ester, 7.1 g of acetoacetic acid allyl ester and 6 ml of concentrated ammonia in 50 ml of methanol for 8 hours yielded 2,6-dimethyl-4-(2'-fluorophenyl)-1,4-dihydropyridine-3,5-dicarboxylic acid 3-methyl ester-5-allyl ester of melting point 130° (from ethanol). Yield 61% of theory.

EXAMPLE 4

Boiling a solution of 14.3 g of 2'-trifluoromethylbenzylideneacetoacetic acid ethyl ester and 7.0 g of β-amino-crotonic acid propargyl ester in 50 ml of ethanol for 10 hours yielded 2,6-dimethyl-4-(2'-trifluoromethylphenyl)-1,4-dihydropyridine-3,5-dicarboxylic acid 3-ethyl ester-5-propargyl ester of melting point 130° (from methanol). Yield 49% of theory.

EXAMPLE 5

Heating a solution of 14.9 of 2'-trifluoromethylbenzylideneacetoacetic acid allyl ester and 6.5 g of β-amino-crotonic acid ethyl ester in 50 ml of ethanol for 8 hours yeilded 2,6-dimethyl-4-(2'-trifluoromethylphenyl)-1,4-dihydropyridine-3,5-dicarboxylic acid 3-ethyl ester-5-allyl ester of melting point 128° (from petroleum ether/ethyl acetate). Yield 57% of theory.

EXAMPLE 6

Heating a solution of 13.6 g of 2'-trifluoromethylbenzylideneacetoacetic acid methyl ester, 7.0 g of acetoacetic acid propargyl ester and 6 ml of concentrated ammonia in 60 ml of isopropanol for 10 hours yielded 2,6-dimethyl-4-(2'-trifluoromethylphenyl)-1,4-dihydropyridine-3,5-dicarboxylic acid 3-methyl ester-5-propargyl ester of melting point 115° (from ethanol). Yield 49% of theory.

EXAMPLE 7

Boiling a solution of 12.4 g of 2'-methoxybenzylideneacetoacetic acid ethyl ester, 9.2 g of acetoacetic acid β-propoxyethyl ester and 6 ml of concentrated ammonia in 50 ml of ethanol for 8 hours yielded 2,6-dimethyl-4-(2'-methoxyphenyl)-1,4-dihydropyridine-3,5-dicarboxylic acid 3-ethyl ester-5-β-propoxyethyl ester of melting point 130° (from petroleum ether/ethyl acetate). Yield 41% of theory.

EXAMPLE 8

Heating a solution of 13.3 g of 2'-chlorobenzylideneacetoacetic acid allyl ester and 6.5 g of β-aminocrotonic acid ethyl ester in 50 ml of ethanol for 8 hours yielded 2,6-dimethyl-4-(2'-chlorophenyl)-1,4-dihydropyridine-3,5-dicarboxylic acid 3-ethyl ester-5-allyl ester of melting point 115° (from petroleum ether/ethyl acetate). Yield 40% of theory.

EXAMPLE 9

Boiling a solution of 15.4 g of 2', 3', 4'-trimethoxybenzylideneacetoacetic acid ethyl ester, 7.1 g of acetoacetic acid allyl ester and 6 ml of concentrated ammonia in 40 ml of ethanol for 10 hours yielded 2,6-dimethyl-4-(2', 3', 4'-trimethoxyphenyl)-1,4-dihydropyridine-3,5-dicarboxylic acid 3-ethyl ester-5-allyl ester of melting point 134°–135° (from ethanol). Yield 58% of theory.

EXAMPLE 10

Heating a solution of 17.2 g of 3', 4'-dimethoxy-5'-bromobenzylideneacetoacetic acid methyl ester and 7.1 g of β-amino-crotonic acid allyl ester in 50 ml of ethanol for 10 hours yielded 2,6-dimethyl-4-(3', 4'-dimethoxy-5-bromophenyl)-1,4-dihydropyridine-3,5-dicarboxylic acid 3-methyl ester-5-allyl ester of melting point 123°–124° (from ethanol/water). Yield 62% of theory.

EXAMPLE 11

After 10 hours' boiling of a solution of 11.7 g 2'-methoxybenzylideneacetoacetic acid methyl ester, 7.0 g acetoacetic acid propargyl ester and 6 ml conc. ammonia in 80 ml ethanol under reflux, 2,6-dimethyl-4-(2'-methoxyphenyl)-1,4-dihydropyridine-3,5-dicarboxylic acid 3-propargyl ester 5-methyl ester of melting point 193°–194°C (acetic ester/petroleum ether) was obtained. Yield 49% of theory.

EXAMPLE 12

By 8 hours' heating of a solution of 3.6 g 2'-trifluoromethylbenzylideneacetoacetic acid methyl ester and 7.0 g β-amino-crotonic acid propargyl ester in 80 ml ethanol, 2,6-dimethyl-4-(2'-trifluoromethylphenyl)-1,4-dihydropyridine 3,5-dicarboxylic acid 3-propargyl ester 5-methyl ester of melting point 111°C was obtained (petroleum ether/acetic ester). Yield 63% of theory.

EXAMPLE 13

After 8 hours' boiling of a solution of 14.3 g 2'-trifluoromethylbenzylideneacetoacetic acid ethyl ester, 6.5 g acetoacetic acid propargyl ester and 6 ml conc. ammonia in 80 ml ethanol, 2,6-dimethyl-4-(2'-trifluoromethylphenyl)-1,4-dihydropyridine-3,5-dicarboxylic acid 3-propargyl ester 5-ethyl ester of freezing point 104°C (acetic ester/petroleum ether) was obtained. Yield 54% of theory.

EXAMPLE 14

By 8 hours' heating of a solution of 12.6 g 2'-chlorobenzylidene acetoacetic acid ethyl ester, 8.0 g acetoacetic acid-β-methoxyethyl ester and 6 ml ammonia in 80 ml ethanol under reflux, 2,6-dimethyl-4-(2'-chlorophenyl)-1,4-dihydropyridine 3,5-dicarboxylic acid 3-β-methoxyethyl ester 5-ethyl ester of melting point 107°–108°C (acetic ester/petroleum ether) was obtained. Yield 54% of theory.

EXAMPLE 15

By 8 hours' boiling of a solution of 15.0 g 3'-trifluoromethylbenzylideneacetoacetic acid isopropylester and 7.1 g amino-crotonic acid allyl ester in 80 ml ethanol, 2,6-dimethyl-4-(3'-trifluoromethyl phenyl)-1,4-dihydropyridine-3,5-dicarboxylic acid 3-isopropyl ester 5-allyl ester of melting point 99°–100°C (acetic ester/petroleum ether) was obtained. Yield 52% of theory.

EXAMPLE 16

After 8 hours' boiling of a solution of 11.1 g 2'-fluorobenzylideneacetoacetic acid methyl ester, 7.0 g acetoacetic acid propargyl ester and 6 ml conc. ammonia in 100 ml ethanol, 2,6-dimethyl-4-(2'-fluorophenyl)-1,4-dihydropyridine-3,5-dicarboxylic acid 3-propargyl ester 5-methyl ester of melting point 142°C (ethanol) was obtained. Yield 67% of theory.

EXAMPLE 17

After 8 hours' heating of a solution of 12.6 g 3'-chlorobenzylidene acetoacetic acid ethyl ester, 7.1 g acetoacetic acid allyl ester and 6 ml conc. ammonia in 80 ml ethanol under reflux, 2,6-dimethyl-4-(3'-chlorophenyl)-1,4-dihydropyridine-3,5-dicarboxylic acid 3-allyl ester 5-ethyl ester of melting point 112°C (acetic ester/petroleum ether) was obtained. Yield 50% of theory.

EXAMPLE 18

After 10 hours' boiling of a solution of 12.4 g 2'-methoxybenzylidene acetoacetic acid ethyl ester, 7.0 g acetoacetic acid ethyl ester, 7.0 g acetoacetic acid propargyl ester and 6 ml conc. ammonia in 60 ml propan-2-ol, 2,6-dimethyl-4-(2'-methoxyphenyl)-1,4-dihydropyridine-3,5-dicarboxylic acid 3-propargyl ester 5-ethyl ester of melting point 113°–114°C (acetic ester/petroleum ether) was obtained. Yield 47% of theory.

EXAMPLE 19

After 8 hours' heating of a solution of 15.0 g 4'-carboxyethylbenzylidene acetoacetic acid propargyl ester and 6.5 g amino-crotonic acid ethyl ester in 50 ml ethanol, 2,6-dimethyl-4-(4'-carboxyethylphenyl)-1,4-dihydropyridine-3,5-dicarboxylic acid 3-propargyl ester 5-ethyl ester of melting point 110°C (ethanol) was obtained. Yield 55% of theory.

EXAMPLE 20

After 6 hours' heating of a solution of 14.7 g 2,4,5-trimethoxybenzylidene acetoacetic acid methyl ester, 7.1 g acetoacetic acid allyl ester and 6 ml conc. ammonia in 100 ml ethanol, 2,6-dimethyl-4-(2', 4', 5'-trimethoxyphenyl)-1,4-dihydropyridine-3,5-dicarboxylic acid 3-allyl ester 5-methyl ester of melting point 98°C (acetic ester/petroleum ether) was obtained. Yield 53% of theory.

What is claimed is:

1. A pharmaceutical composition useful for effecting coronary vascular dilation and for treating hypertension in humans and animals which comprises a coronary vascular dilating amount or an antihypertensive amount of a compound of the formula:

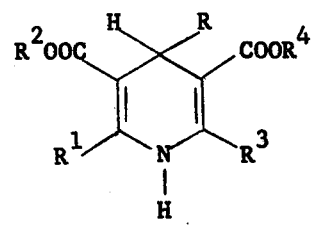

wherein
 R is phenyl, unsubstituted or substituted by a substituent selected from the group consisting of lower alkyl, lower alkoxy, halogeno, trifluoromethyl and carbo(lower alkoxy) or by up to three lower alkoxy or halogeno substituents;
 $R^1$ and $R^3$, independent of the other, is hydrogen, methyl, ethyl or propyl;

R² is a member selected from the group consisting of lower alkyl, allyl, butenyl, propargyl, butynyl and lower alkoxy(lower alkyl);

R⁴ is a member different from R² and is selected from the group consisting of allyl, butenyl, propargyl, butynyl and lower alkoxy(lower alkyl), or a pharmaceutically acceptable acid addition salt thereof, in combination with a pharmaceutically acceptable non-toxic inert carrier.

2. A pharmaceutical composition according to claim 1 wherein each of R¹ and R³ is lower alkyl, R² is lower alkyl and R⁴ is lower alkenyl, lower alkynyl, or lower alkoxy (lower alkyl).

3. A pharmaceutical composition according to claim 2 wherein R¹ and R³ are each methyl, R² is methyl, ethyl, propyl or isopropyl, R⁴ is allyl, propargyl, methoxyethyl or propoxyethyl and R is phenyl substituted by methyl, methoxy, fluoro, chloro, trifluoromethyl or carbo(lower alkoxy).

4. A pharmaceutical composition according to claim 1 wherein the compound is 2,6-dimethyl-4-(2'-methylphenyl)-1,4-dihydropyridine-3,5-dicarboxylic acid 3-ethyl ester-5-allyl ester.

5. A pharmaceutical composition according to claim 1 wherein the compound is 2,6-dimethyl-4-(2'-methylphenyl)-1,4-dihydropyridine-3,5-dicarboxylic acid 3-ethyl ester-5-propargyl ester.

6. A pharmaceutical composition according to claim 1 wherein the compound is 2,6-dimethyl-4-(2'-fluorophenyl)-1,4-dihydropyridine-3,5-dicarboxylic acid 3-methyl ester-5-allyl ester.

7. A pharmaceutical composition according to claim 1 wherein the compound is 2,6-dimethyl-4-(2'-trifluoromethylphenyl)-1,4-dihydropyridine-3,5-dicarboxylic acid 3-ethyl ester-5-propargyl ester.

8. A pharmaceutical composition according to claim 1 wherein the compound is 2,6-dimethyl-4-(2'-trifluoromethylphenyl)-1,4-dihydropyridine-3,5-dicarboxylic acid 3-ethyl ester-5-allyl ester.

9. A pharmaceutical composition according to claim 1 wherein the compound is 2,6-dimethyl-4-(2'-trifluoromethylphenyl)-1,4-dihydropyridine-3,5-dicarboxylic acid 3-methyl ester-5-propargyl ester.

10. A pharmaceutical composition according to claim 1 wherein the compound is 2,6-dimethyl-4-(2'-methoxyphenyl)-1,4-dihydropyridine-3,5-dicarboxylic acid 3-ethyl ester-5-β-propoxyethyl ester.

11. A pharmaceutical composition according to claim 1 wherein the compound is 2,6-dimethyl-4-(2'-chlorophenyl)-1,4-dihydropyridine-3,5-dicarboxylic acid 3-ethyl ester-5-allyl ester.

12. A pharmaceutical composition according to claim 1 wherein the compound is 2,6-dimethyl-4-(2,', 3', 4'-trimethoxyphenyl)-1,4-dihydropyridine-3,5-dicarboxylic acid 3-ethyl ester-5-allyl ester.

13. A pharmaceutical composition according to claim 1 wherein the compound is 2,6-dimethyl-4-(3', 4'-dimethoxy-5-bromophenyl)-1,4-dihydropyridine-3,5-dicarboxylic acid 3-methyl ester-5-allyl ester.

14. A pharmaceutical composition according to claim 1 wherein the compound is 2,6-dimethyl-4-(2'-methoxyphenyl)-1,4-dihydropyridine-3,5-dicarboxylic acid 3-propargyl ester 5-methyl ester.

15. A pharmaceutical composition according to claim 1 wherein the compound is 2,6-dimethyl-4-(2'-trifluoromethylphenyl)-1,4-dihydropyridine 3,5-dicarboxylic acid 3-propargyl ester 5-methyl ester.

16. A pharmaceutical composition according to claim 1 wherein the compound is 2,6-dimethyl-4-(2'-trifluoromethylphenyl)-1,4-dihydropyridine-3,5-dicarboxylic acid 3-propargyl ester 5-ethyl ester.

17. A pharmaceutical composition according to claim 1 wherein the compound is 2,6-dimethyl-4-(2'-chlorophenyl)-1,4-dihydropyridine 3,5-dicarboxylic acid 3-β-methoxyethyl ester 5-ethyl ester.

18. A pharmaceutical composition according to claim 1 wherein the compound is 2,6-dimethyl-4-(3'-trifluoromethylphenyl)-1,4-dihydropyridine-3,5-dicarboxylic acid 3-isopropyl ester 5-allyl ester.

19. A pharmaceutical composition according to claim 1 wherein the compound is 2,6-dimethyl-4-(2'-fluorophenyl)-1,4-dihydropyridine-3,5-dicarboxylic acid 3-propargyl ester 5-methyl ester.

20. A pharmaceutical composition according to claim 1 wherein the compound is 2,6-dimethyl-4-(3'-chlorophenyl)-1,4-dihydropyridine-3,5-dicarboxylic acid 3-allyl ester 5-ethyl ester.

21. A pharmaceutical composition according to claim 1 wherein the compound is 2,6-dimethyl-4-(2'-methoxyphenyl)-1,4-dihydropyridine-3,5-dicarboxylic acid 3-propargyl ester 5-ethyl ester.

22. A pharmaceutical composition according to claim 1 wherein the compound is 2,6-dimethyl-4-(4'-carboxyethylphenyl)-1,4-dihydropyridine-3,5-dicarboxylic acid 3-propargyl ester 5-ethyl ester.

23. A pharmaceutical composition according to claim 1 wherein the compound is 2,6-dimethyl-4-(2', 4', 5'-trimethoxyphenyl)-1,4-dihydropyridine-3,5-dicarboxylic acid 3-allyl ester 5-methyl ester.

24. A method of effecting coronary vascular dilation and treating hypertension in humans and animals which comprises administering to such human or animal a coronary vascular dilating amount or an anti-hypertensive amount of a compound of the formula:

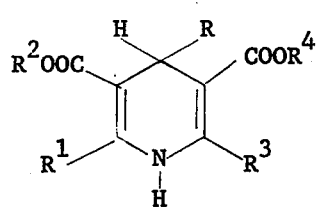

wherein

R is phenyl, unsubstituted or substituted by a substituent selected from the group consisting of lower alkyl, lower alkoxy, halogeno, trifluoromethyl and carbo(lower alkoxy) or by up to three lower alkoxy or halogeno substituents;

R¹ and R³, independent of the other, is hydrogen, methyl, ethyl or propyl;

R² is a member selected from the group consisting of lower alkyl, allyl, butenyl, propargyl, butynyl and lower alkoxy(lower alkyl);

R⁴ is a member different from R² and is selected from the group consisting of allyl, butenyl, propargyl, butynyl and lower alkoxy(lower alkyl), or a pharmaceutically acceptable acid addition salt thereof.

25. A method according to claim 24 wherein R² is lower alkyl and R⁴ is allyl, propargyl or lower alkoxy(lower alkyl).

26. A method according to claim 24 wherein R¹ and R³ are each methyl, R² is methyl, ethyl, propyl or isopropyl, R⁴ is allyl, propargyl, methoxyethyl or propoxyethyl and R is phenyl substituted by methyl, methoxy, fluoro, chloro, trifluoromethyl or carbo(lower alkoxy).

27. A method according to claim 24 wherein the compound is 2,6-dimethyl-4-(2'-methylphenyl)-1,4-dihydropyridine-3,5-dicarboxylic acid 3-ethyl ester-5-allyl ester.

28. A method according to claim 24 wherein the compound is 2,6-dimethyl-4-(2'-methylphenyl)-1,4-dihydropyridine-3,5-dicarboxylic acid 3-ethyl ester-5-propargyl ester.

29. A method according to claim 24 wherein the compound is 2,6-dimethyl-4-(2'-fluorophenyl)-1,4-dihydropyridine-3,5-dicarboxylic acid 3-methyl ester-5-allyl ester.

30. A method according to claim 24 wherein the compound is 2,6-dimethyl-4-(2'-trifluoromethylphenyl)-1,4-dihydropyridine-3,5-dicarboxylic acid 3-ethyl ester-5-propargyl ester.

31. A method according to claim 24 wherein the compound is 2,6-dimethyl-4-(2'-trifluoromethylphenyl)-1,4-dihydropyridine-3,5-dicarboxylic acid 3-ethyl ester-5-allyl ester.

32. A method according to claim 24 wherein the compound is 2,6-dimethyl-4-(2'-trifluoromethylphenyl)-1,4-dihydropyridine-3,5-dicarboxylic acid 3-methyl ester-5-propargyl ester.

33. A method according to claim 24 wherein the compound is 2,6-dimethyl-4-(2'-methoxyphenyl)-1,4-dihydropyridine-3,5-dicarboxylic acid 3-ethyl ester-5-β-propoxyethyl ester.

34. A method according to claim 24 wherein the compound is 2,6-dimethyl-4-(2'-chlorophenyl)-1,4-dihydropyridine-3,5-dicarboxylic acid 3-ethyl ester-5-allyl ester.

35. A method according to claim 24 wherein the compound is 2,6-dimethyl-4-(2', 3', 4'-trimethoxyphenyl)-1,4-dihydropyridine-3,5-dicarboxylic acid 3-ethyl ester-5-allyl ester.

36. A method according to claim 24 wherein the compound is 2,6-dimethyl-4-(3', 4'-dimethoxy-5-bromophenyl)-1,4-dihydropyridine-3,5-dicarboxylic acid 3-methyl ester-5-allyl ester.

37. A method according to claim 24 wherein the compound is 2,6-dimethyl-4-(2'-methoxyphenyl)-1,4-dihydropyridine-3,5-dicarboxylic acid 3-propargyl ester 5-methyl ester.

38. A method according to claim 24 wherein the compound is 2,6-dimethyl-4-(2'-trifluoromethylphenyl)-1,4-dihydropyridine 3,5-dicarboxylic acid 3-propargyl ester 5-methyl ester.

39. A method according to claim 24 wherein the compound is 2,6-dimethyl-4-(2'-trifluoromethylphenyl)-1,4-dihydropyridine-3,5-dicarboxylic acid 3-propargyl ester 5-ethyl ester.

40. A method according to claim 24 wherein the compound is 2,6-dimethyl-4-(2'-chlorophenyl)-1,4-dihydropyridine-3,5-dicarboxylic acid 3-β-methoxyethyl ester 5-ethyl ester.

41. A method according to claim 24 wherein the compound is 2,6-dimethyl-4-(3'-trifluoromethylphenyl)-1,4-dihydropyridine-3,5-dicarboxylic acid 3-isopropyl ester 5-allyl ester.

42. A method according to claim 24 wherein the compound is 2,6-dimethyl-4-(2'-fluorophenyl)-1,4-dihydropyridine-3,5-dicarboxylic acid 3-propargyl ester 5-methyl ester.

43. A method according to claim 24 wherein the compound is 2,6-dimethyl-4-(3'-chlorophenyl)-1,4-dihydropyridine-3,5-dicarboxylic acid 3-allyl ester 5-ethyl ester.

44. A method according to claim 24 wherein the compound is 2,6-dimethyl-4-(2'-methoxyphenyl)-1,4-dihydropyridine-3,5-dicarboxylic acid 3-propargyl ester 5-ethyl ester.

45. A method according to claim 24 wherein the compound is 2,6-dimethyl-4-(4'-carboxyethylphenyl)-1,4-dihydropyridine-3,5-dicarboxylic acid 3-propargyl ester 5-ethyl ester.

46. A method according to claim 24 wherein the compound is 2,6-dimethyl-4-(2', 4', 5'-trimethoxyphenyl)-1,4-dihydropyridine-3,5-dicarboxylic acid 3-allyl ester 5-methyl ester.

* * * * *